United States Patent
Miller et al.

(10) Patent No.: US 6,225,327 B1
(45) Date of Patent: May 1, 2001

(54) COMPOUNDS WHICH INHIBIT HUMAN CONJUNCTIVAL MAST CELL DEGRANULATION FOR TREATING OCULAR ALLERGIC-TYPE COMPLICATIONS

(75) Inventors: Steven T. Miller; Mark R. Hellberg, both of Arlington; John M. Yanni, Burleson, all of TX (US)

(73) Assignees: Alcon Laboratories, Inc., Fort Worth, TX (US); Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/171,045

(22) PCT Filed: Apr. 8, 1997

(86) PCT No.: PCT/US97/06107

§ 371 Date: Oct. 7, 1998

§ 102(e) Date: Oct. 7, 1998

(87) PCT Pub. No.: WO97/38693

PCT Pub. Date: Oct. 23, 1997

Related U.S. Application Data

(60) Provisional application No. 60/015,588, filed on Apr. 18, 1996.

(51) Int. Cl.$^7$ .................................................. A01N 43/40
(52) U.S. Cl. ........................ 514/342; 514/363; 514/464; 514/912
(58) Field of Search ................................. 514/342, 363, 514/464, 912

(56) References Cited

U.S. PATENT DOCUMENTS

| | | |
|---|---|---|
| 3,993,679 | 11/1976 | Hall et al. . |
| 4,778,814 | 10/1988 | Cash . |
| 5,360,720 | 11/1994 | Miller et al. . |

FOREIGN PATENT DOCUMENTS

| | | |
|---|---|---|
| 0 551 626 | 7/1993 | (EP) . |
| WO 91/02497 | 3/1991 | (WO) . |
| WO 92/04008 | 3/1992 | (WO) . |
| WO 93/11766 | 6/1993 | (WO) . |
| WO 93/23082 | 11/1993 | (WO) . |
| WO 95/34299 | 12/1995 | (WO) . |
| WO 96/03985 | 2/1996 | (WO) . |
| WO 97/20806 | 6/1997 | (WO) . |
| WO 97/38693 | 10/1997 | (WO) . |
| 906583 | 8/1990 | (ZA) . |

OTHER PUBLICATIONS

Church, Is Inhibition of Mast Cell Mediator Release Relevant to the Clinical Acitivity of Anti–Allergic Drugs!, *Agents and Actions*, vol. 18, ¾, pp. 288–293 (1986).

Clegg et al., Histamine secretion from human skin slices induced by anti–IgE and artificial secretagogues and the effects of sodium cromoglycate and salbutamol, *Clinical Allergy*, vol. 15, pp. 321–328 (1985).

*Goodman and Gillman's the Pharmacological Basis of Terapeutics*, Eighth Edition, Pergamon Press, New York, pp. 575–588 (1990).

Hennawi, M. El, A comparison between 2% and 4% sodium cromoglycate eye drops in the treatment of vernal keratoconjunctivitis, *Current Eye Research*, vol. 2, No. 11, pp. 765–768 (1982/1983).

Irani et al., Mast cell heterogeneity, *Clinical and Experimental Allergy*, vol. 19, pp. 143–155 (1989).

Kim et al., Inhibition of Histamine Release from Dispersed Human Lung and Tonsillar Mast Cells by Nicardipine and Nifedipine, *British Journal of Clinical Pharmacology*, vol. 19, pp. 631–638 (1985).

Leino et al., Clinical Trial Of The Topical Use Of Disodium Cromoglycate In Vernal, Allergic And Chronic Conjunctivitis, *Acta Ophthalmologica*, vol. 58, pp. 121–124 (1980).

Meisler et al., Cromolyn Treatment of Giant Papillary Conjunctivitis, *Archives in Ophthalmology*, vol. 100, pp. 1608–1610 (1982).

Ostler, H. Bruce, Acute Chemotic Reaction to Cromolyni, *Archives in Ophthalmology*, vol. 100, No. 1, pp. 412–413 (1982).

Pearce et al., Effect of Disodium Cromoglycate on Antigen Evoked Histamine Release From Human Skin, *Clinical Experimental Immunology*, vol. 17, pp. 437–440 (1974).

Schwartz et al., Mast Cells, *The Lung: Scientific Foundations*, Raven Press, Ltd., New York, Ch. 3.4.11, pp. 601–616 (1991).

Tanazaki et al., Inhibitory Effect of Nifedipine and Cromolyn Sodium on Skin Reactions and $^{45}$Ca Uptake and Histamine Release in Rat Mast Cells Induced by Various Stimulatory Agents, *International Archives of Allergy and Applied Immunology*, vol. 72, pp. 102–109 (1983).

Watt et al., Protective effect of lodoxamide tromethamine on allergen inhalation challenge, *Journal of Allergy and Clinical Immunology*, vol. 66, No. 4, pp. 286–294 (1980).

Chemical Abstract 117:33669 (1992). Make et al.*

Chemical Abstract 107:211586 (1987) Jenson.*

\* cited by examiner

*Primary Examiner*—Zohreh Fay
(74) *Attorney, Agent, or Firm*—Michael C. Mayo; Patrick M. Ryan

(57) ABSTRACT

Composition and methods for treating ocular allergic reactions are disclosed. In particular, the invention is directed to compounds which inhibit human conjunctival mast cell degranulation.

3 Claims, No Drawings

COMPOUNDS WHICH INHIBIT HUMAN CONJUNCTIVAL MAST CELL DEGRANULATION FOR TREATING OCULAR ALLERGIC-TYPE COMPLICATIONS

This application is a 371 of PCT/US97/06107 filed Apr. 8, 1997. This application claims benefit of Provisional Application 60/015,588 filed Apr. 18, 1996.

This invention relates to compositions comprising compounds which stabilize human conjunctival mast cells. The compositions are used to prevent allergic responses while also treating existing allergic conditions present in the eye. The invention is also directed to methods of preventing and treating allergic responses with the compositions.

BACKGROUND OF THE INVENTION

The eye, particularly the conjunctiva, has a relatively large number of mast cells. When allergens are present, they can bind to immunoglobulins on the surface of these mast cells and trigger the breakdown, or what is known as the degranulation, of the cell. Upon degranulation, mast cell components, including histamine, are released into the environment outside the mast cell. Through a variety of mechanisms, these components can be responsible for symptoms associated with allergic responses such as itching, redness, lid swelling, vasodilatation and chemosis.

Various therapies have been pursued in order to treat the symptoms of allergies. For example, such therapy has included the use of anti-allergics and anti-histamines.

Anti-allergics are compounds which prevent, inhibit or alleviate allergic reactions. Disodium cromoglycate (DSCG) has been used as an anti-allergic to treat allergic conditions such as: vernal, allergic or chronic conjunctivitis (Leino et al., Clinical Trial Of The Topical Use Of Disodium Cromoglycate In Vernal, Allergic And Chronic Conjunctivitis, *Acta Ophthalmologica*, volume 58, pages 121–124, 1980); vernal keratoconjunctivitis (M. El Hennawi, A comparison between 2% and 4% sodium cromoglycate eye drops in the treatment of vernal keratoconjunctivitis, *Current Eye Research*, volume 2, No. 11, pages 765–768, 1982/1983); and giant papillary conjunctivitis (Meisler et al., Cromolyn Treatment of Giant Papillary Conjunctivitis, *Archives in Ophthalmology*, volume 100, pages 1608–1610, 1982). DSCG has been reported to be irritating to some patients (H. Bruce Ostler, Acute Chemotic Reaction to Cromolyni, *Archives in Ophthalmology*, volume 100, No. 1, pages 412–413, 1982). Cyano phenylene dioxamic compounds disclosed generally in U.S. Pat. No. 3,993,679 issued to Hall et al., are also anti-allergic compounds which have been used in preventing allergic reactions resulting in mast cell degranulation. Although these compounds can be anti-allergic, they can also cause eye irritation and systemic side effects; see for example, Watt et al., Protective effect of lodoxamide tromethamine on allergen inhalation challenge, *Journal of Allergy and Clinical Immunology*, volume 66, No. 4, pages 286–294 (1980).

Anti-histamines are compounds which are administered to antagonize the action of histamine, released from mast cells in response to the presence of allergens. As histamine antagonists, they reduce the redness, itching and swelling caused by the action of histamine on the target tissues in the conjunctiva. They serve to prevent or alleviate many of the symptoms which can result from degranulation of mast cells. However, anti-histamines have also been associated with adverse reactions such as diminished alertness, slowed reaction times and somnolence (*Goodman and Gillman's the Pharmacological Basis of Therapeutics*, Eighth Edition, Pergamon Press, New York, pages 575–588 (1990)).

In order to ascertain compounds with specific mast cell stabilizing efficacy, studies have been conducted with various mast cell lines. However, mast cells differ between species. For example, it is now well established that the types of mast cells which exist in rodents are different from those in humans. See, for example, *THE LUNG: Scientific Foundations*, Raven Press, Ltd., New York, Ch. 3.4.11 (1991). Moreover, mast cell populations of various tissues within the same species differ in phenotype, biochemical properties, functional and pharmacological responses and ontogeny. These recognized differences in mast cells, both between and within species, are referred to as mast cell heterogeneity. See, for example, Irani et al., Mast Cell Heterogeneity, *Clinical and Experimental Allergy*, volume 19, pages 143–155 (1989). Because different mast cells exhibit different responses to pharmacological agents, it is not obvious that compounds claimed to be anti-allergic ("mast cell stabilizers") will have clinical utility in specific mast cell populations. The assumption that mast cells are a homogeneous population, and that experiments in rat mast cells would be predictive of those in human cells, is also known to be incorrect (Church, Is Inhibition of Mast Cell Mediator Release Relevant to the Clinical Activity of Anti-Allergic Drugs?, *Agents and Actions*, volume 18, 3/4, pages 288–293, (1986)).

Examples exist in the art in which mast cell stabilizing drugs inhibit only select populations of mast cells. Disodium cromoglycate is an anti-allergic drug whose local effects are believed to be due to inhibition of mast cell degranulation (Church, Agents and Actions, at 288). This drug was shown to inhibit rodent mast cell degranulation. In human trials, 100 $\mu$M of the drug inhibited mast cells obtained from bronchoalveolar lavage fluid. In dispersed human lung mast cell preparations, 1000 $\mu$M of the drug was required to inhibit only 25% to 33% of histamine release. Finally, histamine release from human skin mast cells was not inhibited at all by disodium cromoglycate. Pearce et al., Effect of Disodium Cromoglycate on Antigen Evoked Histamine Release from Human Skin, *Clinical Experimental Immunology*, volume 17, pages 437–440 (1974); and Clegg et al., Histamine Secretion from Human Skin Slices Induced by Anti-IgE and Artificial Secretagogues and the Effects of Sodium Cromoglycate and Salbutamol, *Clinical Allergy*, volume 15, pages 321–328 (1985). These data clearly indicate that one can not predict with certainty that drugs which possess inhibitory effects on one mast cell population will affect all mast cell populations.

One disadvantage to the ophthalmic use of reported anti-allergic drugs which in fact have no stabilizing effect on human conjunctival mast cells is an increased dosage frequency. Because the effectiveness of ophthalmic formulations containing drugs which do not have conjunctival mast cell activity stems primarily from a simple irrigation effect, more frequent doses are typically required than for drugs which do inhibit conjunctival mast cell degranulation. Therefore, topical ophthalmic formulations which contain drugs having conjunctival mast cell activity may only need to be applied once every 12–24 hours instead of once every 2–4 hours.

Dihydropyridines, such as nicardipine and nifedipine have been disclosed in the art to inhibit histamine release from rat mast cells (Tanazaki et al., Inhibitory Effect of Nifedipine and Cromolyn Sodium on Skin Reactions and $^{45}$Ca Uptake and Histamine Release in Rat Mast Cells Induced by Various Stimulatory Agents, *International Archives of Allergy and Applied Immunology*, volume 72, pages 102–109 (1983)), and to inhibit histamine release from human lung and tonsillar cells (Kim et al., Inhibition of Histamine Release from Dispersed Human Lung and Tonsillar Mast Cells by Nicardipine and Nifedipine, *British Journal of Clinical Pharmacology*, volume 19, pages 631–638 (1985)). Nowhere in the art, however, has it been disclosed to use these types of drugs to stabilize human conjunctival mast cells.

What is needed are drug compounds to prevent the release of mediators of allergic response from the mast cells of the human conjunctiva, the target cells for treating allergic eye diseases. What is also needed are local administration methods for the treatment of allergic eye disease. Furthermore, what is needed are prophylactic therapies in contrast with symptom treating approaches.

SUMMARY OF THE INVENTION

The present invention provides improved ophthalmic compositions comprising a compound which inhibits human conjunctival mast cell degranulation. These compositions may be used to prevent allergic and inflammatory responses by stabilizing the mast cells of the eye, thereby inhibiting the allergic reaction and ocular irritation.

The present invention also provides methods for preventing and treating ophthalmic allergic conditions through administration of the disclosed compositions.

DETAILED DESCRIPTION OF THE INVENTION

The compounds of the present invention inhibit human conjunctival mast cell degranulation. While mast cells exist in various tissues and species, there is considerable mast cell heterogeneity within these different sources. Therefore, in order to provide compounds of the present invention which are specific for human conjunctival mast cells, drug compounds need to be tested for inhibition of human conjunctival mast cell degranulation using human conjunctival mast cells. Such efficacy can be determined by using the method described in U.S. Pat. No. 5,360,720 (Miller et al., "Miller Test"), the entire contents of which are incorporated herein by reference. Briefly, the Miller Test is generally performed by the following protocol:

Tissue Preparation

Human conjunctival tissue is obtained from organ/tissue donors. Tissue is transferred from the transport medium to a suitable buffer for enzymatic treatment.

Enzymatic digestion is preferably accomplished in two stages. During the first stage, the tissue is incubated with a relatively small amount of enzyme or enzyme mixture (generally collegenase (Type IV) and hyaluroniduse (Type I-S)).

Intact tissue is then placed in buffer for second stage digestion. The enzyme or enzyme mixture of this second stage is on the order of ten times the unit concentration as the first stage. The filtrate obtained from each digestion is centrifuged and the pelleted cells resuspended in buffer, preferably calcium/magnesium free buffer. Pooled cells from all digestions are then enriched for mast cells. Generally, the enrichment/cell separation method used in the centrifugation of the filtrate is a single band of Percoll® of about 1.058 g/L. Enriched mast cells are resuspended and washed in buffer.

Equilibration Prior to Treatment or Challenge

The preparations containing the mast cells are then placed in a culture medium, preferably supplemented RPMI 1640, and allowed to equilibrate at about 30°–37° C. for a minimum of about 40 hours.

After equilibrating for a minimum of about 40 hours, the cells may be harvested from the culture (for example, by gentle flushing utilizing pasteur pipettes), pooled and centrifuged. Cell pellets may then be resuspended in buffer and viability and mast cell number determined by well known methods. The conjunctival mast cells are now prepared for use in mast cell stabilization assays.

Mast Cell Stabilization Assay

Mast cells (5000/tube; 1 mL final volume) were challenged (37° C.) for 15 minutes with anti-human IgE (10 µg/mL) following a 15 minute treatment (37° C.) with the compound of interest or buffer. The reaction was terminated by centrifugation (500239 ×g, 4° C., for 10 minutes). Supernatents were stored at −20° C. until analyzed for histamine content by radioaminoassay (RIA). The $IC_{50}$ of each compound (concentration at which 50% of the histamine release was inhibited, as compared to control) was then calculated.

Using the Miller Test, compounds which exhibit an $IC_{50}$ value of 100 µM or less are considered to be superior agents, and are therefore Human Conjunctival Mast Cell Stabilizers ("HCMCS") of the present invention. Preferred compounds of the present invention will exhibit an $IC_{50}$ value of 30 µM or less.

The compounds of the present invention meet the preceding HCMCS definition and have the following formula (I):

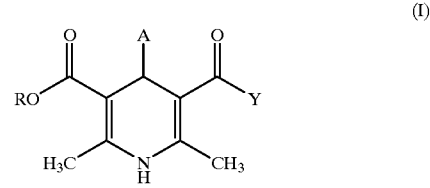

wherein:

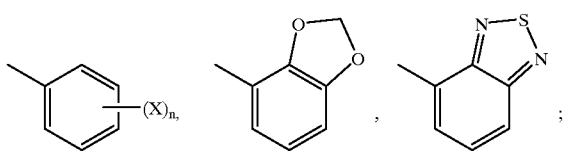

A is n is 1 or 2;

when n is 1,

X is H, halogen, $CF_3$, alkyne, $-S(O)_{n'}R$, OR or $NO_2$;

when n is 2,

X is H or halogen;

n' is 0, 1 or 2;

R is $C_1$–$C_5$ (un)branched alkyl;

Y is $Z(C(R')(R'))_{n''}Z'$ or

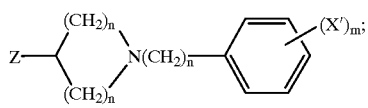

wherein:
n" is 2 to 4;
m is 0, 1, 2, 3;
R' is H or R;
X' is H, halogen, $CF_3$, alkyne, $-S(O)_nR$, OR or $NO_2$;
Z is NH or O;
Z' is N(R')(R") or

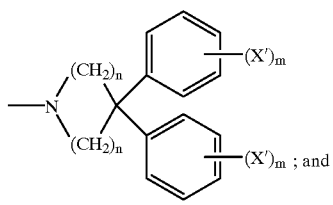

R" is

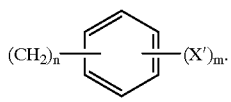

Preferred components are those wherein,
n" is 2;
R' is H, $CH_3$
X is $NO_2$; and
X' is H.

Preferred compounds include nicardipine, barnidipine, YC-114, elgodipine, niguldipine and R(-)-niguldipine.

The most preferred compounds are nicardipine and niguldipine.

The compounds of the present invention contain an asymmetric center and therefore can exist as enantiomers. It is understood that the scope of the present invention covers all such isomers. The compounds of the present invention also include non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartric acid and phosphoric acid.

The compounds of the present invention are generally available from commercial sources, or may be synthesized by methods known to those skilled in the art of organic chemistry.

Some of the compounds of the present invention possess calcium channel blocking activity. It is to be appreciated, however, that the human conjunctival mast cell degranulation efficacy of the compounds of the present invention is unrelated to calcium channel blocking efficacy. For example, the dihydropyridine calcium channel blockers, nitrendipine, nimodipine, isradipine and nifedipine, show markedly less activity ($IC_{50}$ above 300 $\mu M$) in the Miller Test, and thus, do not meet the functional criteria of compounds of the present invention. Thus, it has unexpectedly been found that a defined subset of dihydropyridine compounds are superior human conjunctival mast cell stabilizers.

The compounds of the present invention are useful in treating allergic conditions and reactions of the eye. The preferred route of administration is topical. As used herein, the term "pharmaceutically effective amount" refers to that amount of an HCMCS which ameliorates allergic conditions/reactions of the eye. For example, a pharmaceutically effective amount of a compound of the present invention will ameliorate conditions resulting from conjunctival mast cell histamine release. The compounds of the present invention can be administered as solutions, suspensions, or emulsions (dispersions) in a pharmaceutically acceptable ophthalmic vehicle.

In forming compositions for topical administration, the compounds of the present invention are generally formulated between about 0.001 to about 2 percent by weight (wt %) solutions in water at a pH between 5 to 8. The compounds are preferably formulated between about 0.01 to about 2 wt % and, most preferably, between about 0.1 and about 1 wt %. While the precise regimen is left to the discretion of the clinician, it is recommended that the resulting solution or solution suspensions be topically applied by placing one drop of a solution(s)/suspension(s) in each eye 1 or 2 times a day.

Other ingredients which may be desirable to use in the ophthalmic preparations of the present invention include preservatives, co-solvents and viscosity building agents. As used herein, the term "pharmaceutically acceptable ophthalmic vehicle" refers to those vehicles which cause at most, little to no ocular irritation, provide suitable preservation if needed, and deliver the HCMCS in a homogenous dosage.

Preferred formulations of the compounds of the present invention include the following Examples 1–3:

EXAMPLE 1

| Ingredient | Amount (wt %) |
| --- | --- |
| Nicardipine | 0.001–0.1% |
| Phosphate Buffered Saline | 1.0 |
| Benzalkonium Chloride | 0.01 |
| Polysorbate 80 | 0.5 |
| Purified water | q.s. to 100% |

EXAMPLE 2

| Ingredient | Amount (wt %) |
| --- | --- |
| Niguldipine | 0.001–0.1% |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 3

| Ingredient | Amount (wt %) |
|---|---|
| Barnidipine | 0.001–0.1% |
| Phosphate Buffered Saline | 1.0 |
| Hydroxypropyl-β-cyclodextrin | 4.0 |
| Purified water | q.s. to 100% |

What is claimed is:

1. A method of alleviating ocular allergic reactions involving conjunctival mast cell degranulation which comprises topically administering a composition comprising a pharmaceutically effective amount of a human conjunctival mast cell stabilizer having a structure according to formula (I) in a pharmaceutically acceptable ophthalmic vehicle:

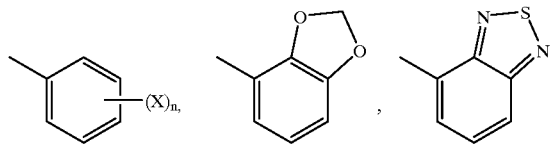
(I)

wherein:
A is

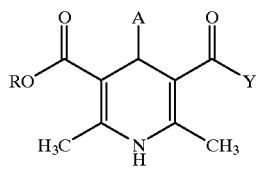

n is 1 or 2;
when n is 1,
X is H, halogen, $CF_3$, alkyne, —$S(O)_n R$, OR or $NO_2$;
when n is 2,
X is H or halogen;
n' is 0, 1 or 2;
R is $C_1$–$C_5$ (un)branched alkyl;
Y is $Z(C(R')(R'))_{n''}Z'$ or

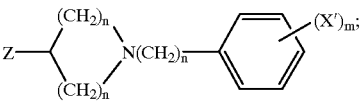

wherein:
n" is 2 to 4;
m is 0, 1, 2, 3;
R' is H or R;
X' is H, halogen, $CF_3$, alkyne, —$S(O)_n R$, OR or $NO_2$;
Z is NH or O;
Z' is N(R')(R") or

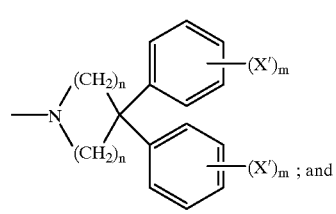
; and

R" is

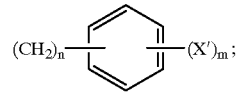;

provided that the human conjunctival mast cell stabilizer is not nicardipine.

2. A method according to claim 1, wherein the compound is selected from the group consisting of nicardipine, barnidipine, YC-114, elgodipine, niguldipine and R(-)-niguldipine.

3. A method according to claim 2, wherein the compound is niguldipine.

* * * * *